United States Patent [19]

Tokumaru

[11] Patent Number: 4,726,684

[45] Date of Patent: Feb. 23, 1988

[54] MEASUREMENT APPARATUS FOR OPTICAL TRANSMISSION FACTOR

[75] Inventor: Syokichi Tokumaru, Tokyo, Japan

[73] Assignee: OKI Electric Industry Co., Ltd., Tokyo, Japan

[21] Appl. No.: 946,520

[22] Filed: Dec. 24, 1986

Related U.S. Application Data

[63] Continuation of Ser. No. 631,615, Jul. 17, 1984, abandoned.

[30] Foreign Application Priority Data

Jul. 22, 1983 [JP] Japan ............... 58-132692
Jul. 22, 1983 [JP] Japan ............... 58-132691

[51] Int. Cl.⁴ .............................................. G01N 21/59
[52] U.S. Cl. ............................... 356/435; 350/394; 350/173; 356/437
[58] Field of Search ............ 356/436, 438, 439, 442, 356/434, 435, 437; 350/173, 397

[56] References Cited

U.S. PATENT DOCUMENTS 3,872,315  3/1975  Boll ........................ 356/439 X

FOREIGN PATENT DOCUMENTS 2152631  5/1973  Fed. Rep. of Germany ...... 350/394

Primary Examiner—Vincent P. McGraw
Attorney, Agent, or Firm—Martin M. Novack

[57] ABSTRACT

An optical transmission factor is measured by using mutual measuring technology having a pair of identical units (44, 50) located on opposite sides of an object (A). Each of said units (44, 50) comprises a pair of beam splitters (47, 48), a light source means (45, 46) for illuminating an object (A) through a first beam splitter (47) and providing offset beam (56) from said first beam splitter (47), a photo-detector (49) for converting optical power from the other unit (50) and said offset beam (56), wherein each of said beam splitters (47, 48) is substantially in parallelogram shape with two pairs of confronting planes (24, 25; and 22, 23), first pairs of planes (24, 25) are not perpendicular to the second pair of planes (22, 23), one of first pair of planes (24) is mirror coated for reflecting the inside beam, so that split beams (29, 31) from single beam (27) share a common point (200) on the plane (23). Thus, a dust/soil free measurement with no mechanically moving means is accomplished.

8 Claims, 9 Drawing Figures

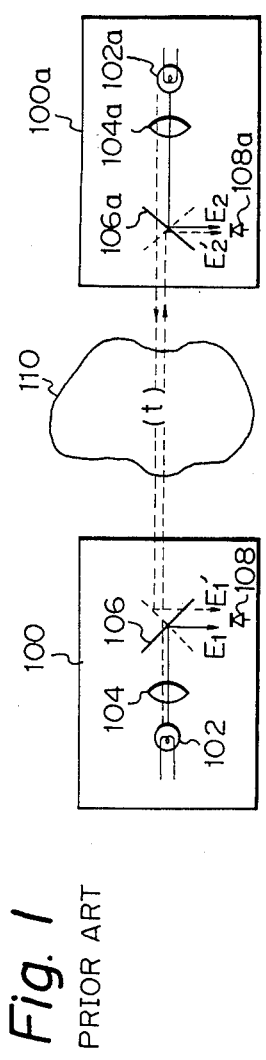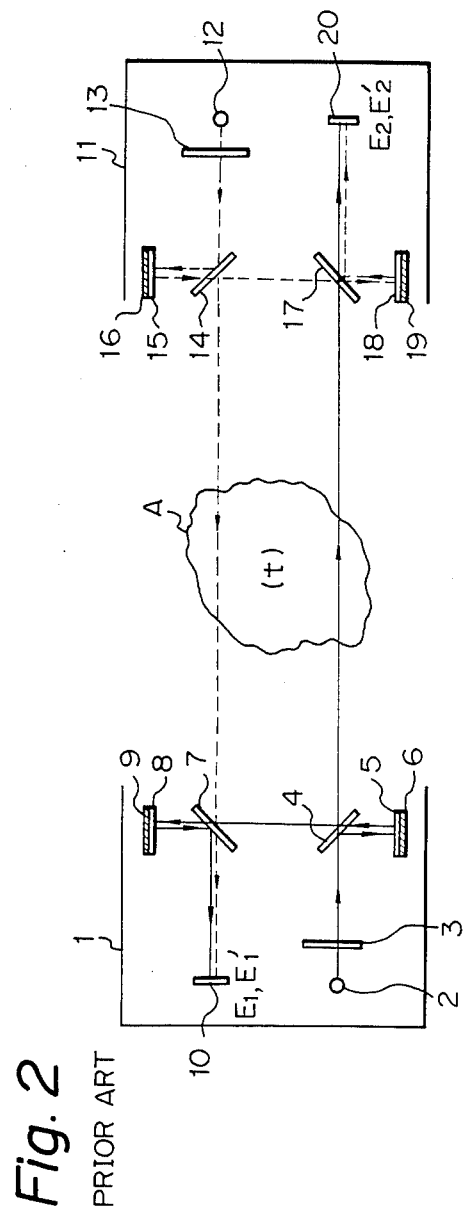
Fig. 1 PRIOR ART
Fig. 2 PRIOR ART

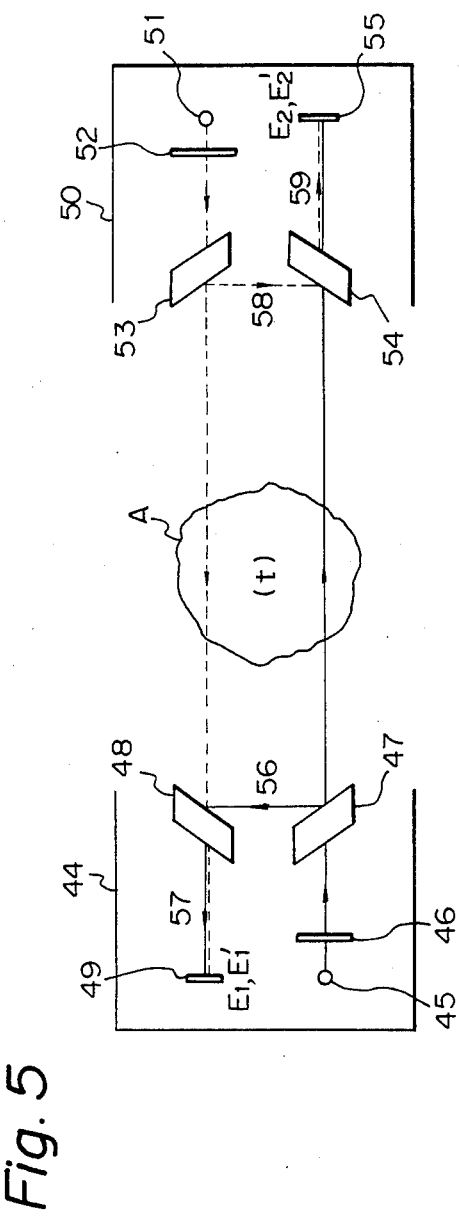
Fig. 5
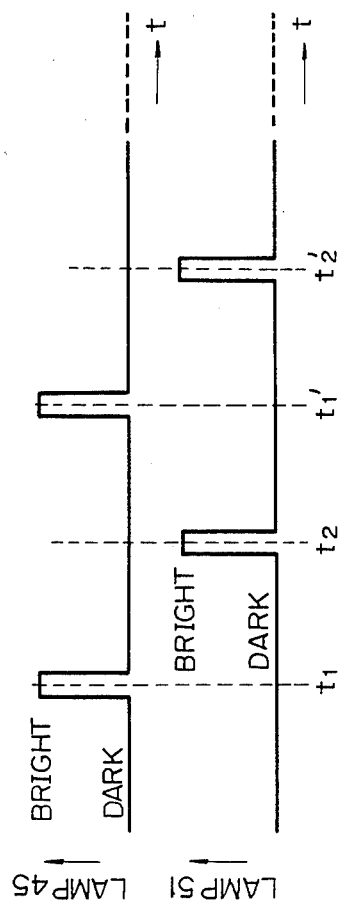
Fig. 6(a)
Fig. 6(b)

MEASUREMENT APPARATUS FOR OPTICAL TRANSMISSION FACTOR

This is a continuation of U.S. application Ser. No. 631,615, filed July 17, 1984, now abandoned.

BACKGROUND OF THE INVENTION

The present invention relates to a measurement apparatus of optical transmission factor and, in particular, relates to such an apparatus which has no mechanical moving means. The present invention uses the particular structure of an optical beam splitter. The present invention has application, for instance in, a smoke indicator, a dust concentration indicator, a gas combustion control, etc.

The principle of measuring the optical transmission factor is to use a light source and a light detector. When the strength of the light is $I_0$, and the strength of that light when the light passes the object which absorbs some of the light energy is I, the transmission factor T of that object is defined as, $T = I/I_0$.

However, the direct application of that principle is not preferable, since it is subject to measurement error due to soil and/or dust on a window of the measurement apparatus.

A dust/soil free apparatus of a prior art is shown in our previous Japanese patent application No. 208550/82 as shown in FIGS. 1 and 2. In FIG. 1, the numerals 100 and 100a are measurement apparatus units, 102 and 102a are lamps, 104 and 104a are lenses, 106 and 106a are rotation mirrors, 108 and 108a are optical detectors, and 110 is an object for measuring transmission factor (t). When the mirrors 106 and 106a are at the position indicated by the solid line, then, the light from the lamp 102 is reflected by the mirror 106, and is applied to the detector 108, which provides the output voltage $E_1$. Similarly, the light from the lamp 102a is reflected by the mirror 106a, and is applied to the detector 108a, which provides the output voltage $E_2$. $E_1$ and $E_2$ are expressed as follows.

$$E_1 = I_1 m_1 g_1$$

$$E_2 = I_2 m_2 g_2$$

where $I_1$ and $I_2$ are values showing the strength of the light of the lamps 102 and 102a, respectively, $m_1$ and $m_2$ are constants relating to the characteristics of the mirrors 106 and 106a, respectively, and $g_1$ and $g_2$ are also constants defined by the sensitivity of the detectors 108 and 108a, respectively.

Similarly, when the mirror 106 is at the position indicated by the dotted line position, and the mirror 106a is at the position which does not prevent a light beam, the light from the lamp 102a passes through the object 110 which has the transmission factor (t), then, is reflected by the mirror 106, and finally, detected by the detector 108, which provides the output voltage $E_1'$. Similarly, when the mirror 106a is at the dotted line position, and the other mirror 106 does not prevent the beam from the lamp 102, the light beam from the lamp 102 passes through the object 110, then, is reflected by the mirror 106a, and is detected by the detector 108a, which provides the output voltage $E_2'$. The values $E_1'$ and $E_2'$ are shown below.

$$E_1' = I_2(t) m_1 g_1$$

$$E_2' = I_1(t) m_2 g_2$$

When th following ratio is calculated, the transmission factor (t) is obtained.

$$\sqrt{E_1' E_2'/(E_1 E_2)} = \sqrt{(I_2(t) m_1 g_1 I_1(t) m_2 g_2)/(I_1 m_1 g_1 I_2 m_2 g_2)} = (t)$$

Since the values $E_1$, $E_2$, $E_1'$ and $E_2'$ are not measured at the same time, those values are measured on a time divisional basis according to the rotation of the mirrors.

However, the apparatus of FIG. 1 has the disadvantage that the mirrors must rotate, and the moving mirrors decrease the operational reliability of the apparatus.

FIG. 2 shows a prior at improvement of the apparatus of FIG. 1, and FIG. 2 uses a fixed polarization beam splitter, instead of a rotation mirror.

In FIG. 2, the numerals 1 and 11 are measuring apparatus units, and the object A is located between the apparatus units 1 and 11. Each of the apparatus units 1 and 11 has a light source 2 (12), an interference filter 3 (13), a first polarization beam splitter 4 (14), a first quarter wavelength plate 5 (15), a first reflection mirror 6 (16), a second polarization beam splitter 7 (17), a second quarter wavelength plate 8 (18), a second reflection mirror 9 (19), and a photo-detector 10 (20). The light source 2 (12) is a tungsten lamp or a light emission diode, and is controlled so that the lamps 2 and 12 provide light output alternately. Accordingly, when the lamp 2 is bright, the lamp 12 is dark. The light beam of the lamp 2 is applied to the interference filter 3, which restricts the range of the wavelength. Then, the beam is applied to the first beam splitter 4, in which the S polarization component is reflected, and the P polarization component passes through and is applied to the object A.

It should be appreciated that S polarization component is reflected by a beam splitter, and P polarization component passes through a beam splitter in the description of the present specification.

When the input beam is a circular polarization beam, the strength of the P polarization component is the same as that of the S polarization component. The reflected S polarization component passes the first quarter wavelength plate 5, reflected by the first reflection mirror 6, passes again the first quarter wavelength plate 5 which converts the polarization to the P polarization. Then, the beam is applied again to the first polarization beam splitter 4 and passes the same, and further is applied to the second polarization beam splitter 7 and passes the same. Then, the beam is applied to the second reflection mirror 9 through the second quarter wavelength plate 8, and is relfected by that mirror. The reflected beam passes again the second quarter wavelength plate 8 again, and is converted to the S polarization beam. The converted S polarization beam is reflected by the second polarization beam splitter 7, and is applied to the photodetector 10 which converts the optical power to the electrical signal $E_1$. On the other hand, the P polarization beam which passes through the beam splitter 4 is applied to the second polarization beam splitter 17 through the object A, and passes that splitter, then, is applied to the photo-detector 20, which provides the output voltage $E_2'$.

When the light source 2 is dark, the light source 12 is bright. The light beam from the light source 12 is applied to the detectors 10 and 20, after passing along the dotted paths, and it is assumed that the detectors 10 and 20 provide the output signals, $E_1'$ and $E_2$, respectively. The transmission factor (t) of the object (A) is obtained by calculating the following equation.

$$(t) = \sqrt{(E_1'E_2')/(E_1E_2)} \tag{1}$$

The structure of FIGS. 1 and 2 has the advantage that the effect of soil and/or dust on a mirror or a polarization beam splitter is automatically compensated.

However, a polarization beam splitter which is a flat plate with a polarization film as shown in FIG. 2 has the disadvantage that the ratio of the reflected beam to the passed beam plus the reflected beam of P polarization component can not be small enough, and therefore, the calculated transmission factor is not accurate. The small ratio of the reflected beam to the passed beam plus the reflected beam of that polarization beam splitter comes from the narrow bandwidth from P component transfer wavelength to S component transfer wavelength of the characteristic curve between the wavelength and the transmissivity. That is to say, only the beam applied to a polarization film of a splitter with the Brewster angle is separated well enough.

The theoretical analysis when said ratio is small, that is to say, when a part of S component passes through a beam splitter, and/or when a part of P component reflects, is described below.

It is assumed in FIG. 2 that all the beam splitters 4, 7, 14 and 17 have the same characteristics as one another, and the leakage of each beam splitter is 10%. That is to say, it is assumed that 10% of S component passes through a beam splitter, and 10% of P component is reflected by a beam splitter, although said leakage is zero in an ideal beam splitter.

Concerning the light beam generated by the light source 2, the 90% of the P component passes through the beam splitter 4, the output of which is applied to the beam splitter 17 through the object A. Said beam splitter 17 also passes 90% of the input beam, and the output of the beam splitter 17 is applied to the detector 20, which provides the electrical signal $E_1' = 0.81(t)$ $(=0.9 \times (t) \times 0.9)$.

The first leakage of that P component is the 10% of P component, which is reflected by the beam splitter 4. That first leakage beam is applied to the photo-detector 10, through the quarter wavelength plate 5, the mirror 6, the quarter wavelength plate 5, the beam splitter 4 (the P component is converted to the S component in passing the quarter wavelength plate 5, and the converted S component passes through the beam splitter 4), the beam splitter 7, the quarter wavelength plate 8, the morror 9, the quarter wavelength plate 8, and the beam splitter 7 (the converted S component is converted again to the P component by the quarter wavelength plate 8, so the re-converted P component is reflected by the beam splitter 7). However, the amount of the leakage in that path is very small, and can be neglected in the analysis.

The second leakage of that P component is the 10% of P component reflected by the beam splitter 17. The second leakage beam is also applied to the detector 10, through the beam splitter 4, the object A, the beam splitter 17 (10%), the beam splitter 14, the object A, and the beam splitter 7. The electrical signal by that second leakage is $0.008(t^2)$ $(=0.9 \times (t) \times 0.1 \times 0.1 \times (t) \times 0.9)$, and said signal is added to the value $E_1$.

On the other hand, concerning the S component which provides the signal $E_1$ in the detector 10, the normal optical path is, through the beam splitter 4(90%), the quarter wavelength plate 5, the mirror 6, the quarter wavelength plate 5, the beam splitter 4 (90%), the beam splitter 7(90%), the quarter wavelength plate 8, the mirror 9, the quarter wavelength plate 8, the beam splitter 7 (90%). Therefore, the signal $E_1$ is 0.66 $(=0.9 \times 0.9 \times 0.9 \times 0.9)$.

The first leakage of that S component is caused by the beam splitter 4 which passes 10% of the S component. The 10% of the leaked S component is, through the object A, the beam splitter 17 (which reflects the S component), the beam splitter 14 (which also reflects the S component), the object A, the beam splitter 7, to the detector 10. The level by that leaksge path of the S component is $0.008(t^2)$ $(=0.1 \times (t) \times 0.9 \times 0.9 \times (t) \times 0.1)$, and that level is added to the signal $E_1$.

The second leakage of the S component is the reflection by the beam splitter 7, however, the amount of the second leakage is small, and can be neglected in the present analysis.

The third leakage of the S component is the path throught the beam splitter 4, the object A, the beam splitter 17, to the detector 20, which provides the signal $0.01(t)$ $(=0.1 \times (t) \times 0.1)$. That signal is added to the $E_1'$.

Accordingly, the level $E_1$ and $E_1'$ considering the leakage is shown below.

$$E_1 = 0.66 + 0.008(t^2) + 0.008(t^2) = 0.66 + 0.016(t^2)$$

$$E_1' = 0.81(t) + 0.01(t) = 0.82(t)$$

Similarly, the similar error occurs relating the beam generated by the light source 12 as follows.

$$E_2 = 0.66 + 0.016(t^2)$$

$$E_2' = 0.82(t)$$

Accordingly, the equation (1) is calculated as follows.

$$\sqrt{(E_1'E_2')/(E_1E_2)} = 0.82(t)/(0.66 + 0.016(t^2))$$

When $t = 1$, said value is;

$$\sqrt{(E_1'E_2')/(E_1E_2)} = 1.21$$

It should be appreceated that said value is preferably 1.0. Therefore, the 21% of error is caused by the leakage of ooptical beam by the beam splitters.

SUMMARY OF THE INVENTION

It is an object, therefore, of the present invention to overcome the disadvantages and limitations of a prior optical transmission factor measuring apparatus by providing a new and improved measuring apparatus for the optical transmission factor.

It is also an object of the present invention to provide a measuring apparatus of the optical transmission factor, which is free from the effect soil an apparatus, does not have mechanically moving means, and provides accurate measured values.

The above and other objects are attained by an optical transmission factor measurement apparatus comprising a pair of identical units locted at opposite sides of an object to be measured, each unit comprises means for generating light beams having a predetermined restricted wavelength band so that the light beam of each unit is generated alternately, a first beam splitter which passes through a first polarization beam of said light beam to an object, and offsets a second polarization beam, a second beam splitter which combines said offset beam by said first beam splitter, and a beam from another unit through an object, to a single common beam, a photo-detector to receive said combined common beam to provide an electrical signal relating to intensity of said common optical beam, wherein each of said beam splitters is substantially parallelogramic having a first pair of confronting planes for input and output of an optical beam, a second pair of confronting planes, and a polarization film located along a diagonal plane of the beam splitter, and one of said second confronting planes has a mirror surface for reflecting the inside optical beam.

BRIEF DESCRIPTION OF THE DRAWINGS

The foregoing and other objects, features, and attendant advantages of the present invention will be appreciated as the same become better understood by means of the following description and accompanying drawings wherein;

FIG. 1 shows a structure of a prior measuring apparatus of the optical transmission factor, FIG. 2 is another structure of a prior measuring apparatus of the optical transmission factor, FIG. 5 shows the structure of the measuring apparatus of optical transmission factor according to the present invention, FIGS. 6(a) and 6(b) show time sequence of light sources in FIG. 5.

DESCRIPTION OF THE PREFERRED EMBODIMENTS

The important feature of the present invention is the use of the particular structure of a polarization beam splitter, which is described first.

Figure 3:
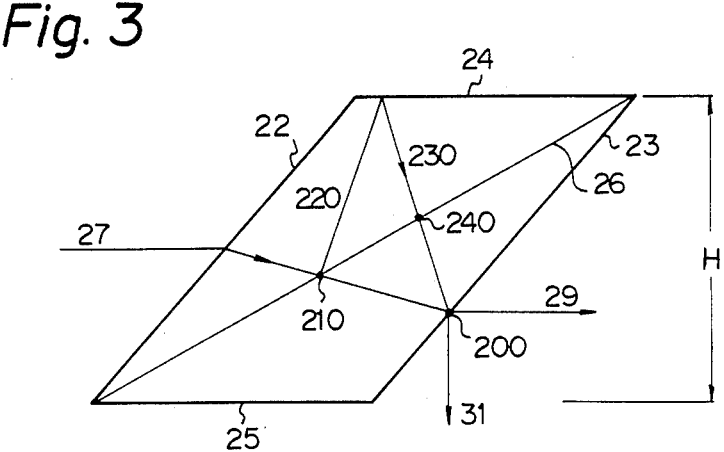
FIG. 3 shows structure of a parallelogramic beam splitter which is used in the present invention.

FIG. 3 shows the structure of the cross section of the polarization beam splitter, which is parallelogramic as shown in the figure. The plane 22 is parallel with the plane 23, and the plane 24 is parallel with the plane 25. The length perpendicular to the drawing is almost the same as the height H of the parallelogram.

A reflection film is attached inside of the plane 24.

A polarization film 26 is provided along the diagonal plane of the parallelogram, as in the case of a conventional cubic beam splitter.

It is assumed that an input beam 27 which is a circular polarization beam is applied to the plane 22 so that the beam 27 is parallel to the plane 25 (or the plane 24), then, the beam 27 is refracted at the plane 22, due to the difference of the refraction index between the material of the beam splitter and air space, then, the beam is applied to the point 210 on the polarization film 26. The P polarization component of the beam passes through the polarization film 26, and goes out of the beam splitter at the point 200 on the plane 23. The output beam 29 generated at the point 200 is parallel with the input beam 27. On the other hand, the S polarization component at the point 210 is reflected by the polarization film 26, then, the reflected beam is applied to the mirror surface of the plane 24 through the path 220. The mirror surface of the plane 24 reflects the input beam, and the reflected beam is applied again to the polarization film 26 through the path 230. The beam along the path 230 is applied to the point 240 on the polarization film 26, and said beam passes the film 26, but is not reflected by that film 26. The reason why the S polarization component is reflected at the point 210, while that S polarization component passes through the film at the point 240, is due to the angle of incidence. The incidence angle at the first point 210 is selected to be close to the Brewster angle, and the incidence angle at the point 240 is smaller or almost perpendicular as shown in the figure. The beam passing through the polarization film 26 at the point 240 is applied to the plane 23, then, goes out of the beam splitter along the path 31. The output beam 29 is perpendicular to the output beam 31.

Further, the parallelogramic beam splitter and the input point of the beam is designed so that the output point 200 on the plane 23 for the first P polarization beam which passes through the polarization film 26 coincides with the output point for the second S polarization beam. That is to say, both the P polarization beam which passes through the polarization film and the S polarization beam which is reflected by the polarization film passes the common point 200 on the output plane 23, while the output beam 29, is perpendicular to the output beam 31.

Figure 8:
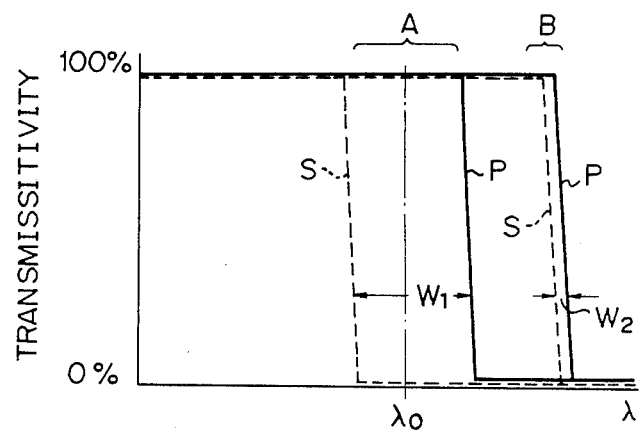
FIG. 8 shows the characteristic curves of a beam splitter.

The reason why the S polarization component is reflected at the pooint 210, while the S component passes the film at the point 240 is described in accordance with FIG. 8, which show the characteristics of a beam splitter. In FIG. 8, the horizontal axis shows the wavelength of a beam, and the vertical axis shows the transmissitivity (transmission factor) of a beam splitter. The transmissivity 100% means that an input beam passes through the beam splitter, and the transmissity 0% means that the input beam is reflected by the beam splitter. The solid lines in the figure show the characteristics of the P polarization component, and the dotted lines show the S polarization component.

It should be noted in FIG. 8 that the transfer wavelength in which the P component changes the transmissity from 100% to 0% is longer than the transfer wavelength in which the S component changes the transmissitivity from 100% to 0%, and that the transfer wavelength of both the P component and the S component shifts to the longer wavelength when the angle of incidence is small. In FIG. 8, the symbol A shows the case when the angle of incidence is close to the Brewster angle, and the symbol B shows the case when the angle of incidence is small. Further, it should be noted in FIG. 8 that the wavelength band $W_1$ in case of Brewster angle is wider than the wavelength band $W_2$ in case of small incidence angle. The Brewster angle is defined by the structure of a beam splitter (glass and polarization film).

Accordingly, a beam splitter is usually used so that the angle of incidence is close to the Brewster angle, and the wavelength of the input beam is ($\lambda_0$) which is the center of the wavelength band $W_1$.

In FIG. 3, it is assumed that the angle of incidence at the point 210 is close to the Brewster angle, or at least, the bandwidth $W_1$ between the P component transfer wavelength and the S component transfer wavelength is sufficiently wide, and the wavelength of the input beam is close to the center of that wavelength band. Accordingly, the P component passes through the point 210, and the S component is reflected at that point 210. On the other hand, at the point 240 where the S component which is reflected by the mirror surface of the plane 24 is applied, the angle of incidence of the input beam is small, and therefore, the transfer wavelength of the S component is longer than the wavelength of the input beam, as shown in the symbol B of FIG. 8. Accordingly, both the S component and the P component with the wavelength ($\lambda_0$) passes through the point 240.

The typical design of a beam splitter which has the feature of FIG. 3 is as follows:

The refraction index of a splitter body (glass); 1.684

The angle between the plane 25 and the film 26; 24°48′

The angle between the plane 24 and the film 26; 24°48′

The angle between the plane 22 and the film 26; 22°12′

The angle between the plane 23 and the film 26; 22°12′

Figure 4:
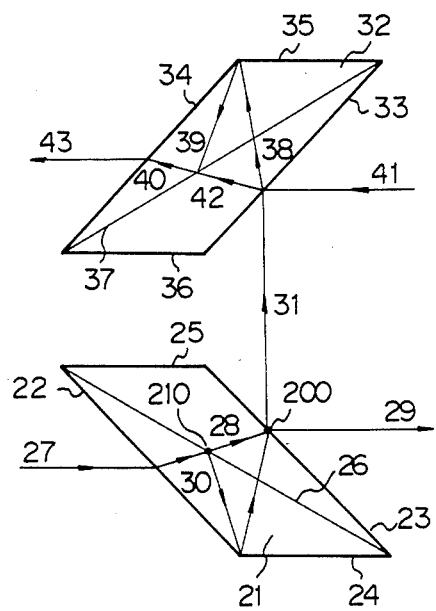
FIG. 4 shows the operation of the parallelogramic beam splitter in the transmission factor measuring apparatus according to the present invention.

FIG. 4 shows the combination of a pair of polarization beam splitters each of which has the structure of FIG. 3. In FIG. 4, the first beam splitter 21 separates the input beam 27 into the P polarization output beam 29, and the S polarization output beam 31 which is perpendicular to said P output beam 29. The second beam splitter 32 combines a pair of input beams 31 and 41 and provides a common output beam 43.

The first beam splitter 21 has a pair of parallel planes 22 and 23, and 24 and 25. The polarization film (dielectric film) 26 is located along the diagonal plane of the parallelogram, and the reflection mirror is provided inside of the plane 24.

The input beam 27, which may be either a circular polarization beam, or a linear polarization beam with 45° relating to upright line, is applied to the plane 22, then, is separated to P polarization component and S polarization component by the polarization film 26. The P component passes through the polarization film 26, goes along the path 28, and output as the beam 29. The output beam 29 is parallel to the input beam 27. The S polarization beam separated from the input beam 27 is reflected by the polarization film 26, goes along the path 30, then, is reflected by the mirror surface 24 and is applied again to the polarization film 26. As the angle of incidence at this time is small, the beam reflected by the mirror surface 24 passes through the polarization film 26, and becomes the output beam 31 which is perpendicular to another output beam 29.

It is assumed of course that the angle of incidence of the input beam applied the polarization film 26 is close to the Brewster angle which is defined by the structure and the material of the beam splitter, or at least said angle of incidence is within 5° from the Brewster angle.

The second beam splitter 32 has the same structure as that of the first one 21. The plane 33 is parallel with the plane 34, and the plane 35 is parallel with the plane 36. The polarization film 37 is provided along the diagonal plane of the parallelogram. The second beam splitter 32 is located so that the plane 36 is parallel with the plane 25, and the plane 33 faces with the plane 23.

The path of the beam in the second beam splitter 32 is opposite to that of the first beam splitter 21. The input beam 31 to the second beam splitter 32 is applied to the plane 33 from the first beam splitter 21, and said beam 31 goes along the path 38, passes through the polarization film 37, is reflected by the mirror surface 35, and returns to the polarization film 37 along the path 39. The beam along the path 39 is reflected by the polarization film 37 because of the incidence angle close to the Brewster angle, and becomes the output beam 43 through the path 40. The input beam 41 (P component) to the plane 33 passes through the polarization film 37 through the path 42, and joins the output beam 43 through the path 40. It should be appreciated that both the input beams 31 and 41 provide the single common output beam 43, due to the particular structure of the beam splitter, and the particular location of the input beams.

FIG. 5 shows the structure of the measuring apparatus of the optical transmission factor according to the present invention. In the figure, the first unit 44 has the completely same structure as the second unit 50, and the object A which the optical transmission factor is subject to be measured is positioned between the units 44 and 50. The unit 44 (50) has a light source 45 (51), an interference filter 46 (52), a first polarization beam splitter 47 (53), a second polarization beam splitter 48 (54), and a photo-detector 49 (55). The light source 45 (or 51) may be a tungsten lamp, a light emission diode, or a laser diode. The light sources 45 and 51 provide an optical beam alternately as shown in FIG. 6. That is to say, when the first light source 45 is bright, the second light source 51 is dark.

The beam from the light source 45 is applied to the interference filter 46, which restricts the wavelength band (when a laser diode is used as a light source, the interference filter 46 may be removed, as the wavelength band of a laser beam is inherently narrow). Thus, the beam of the light source 45 is applied to the polarization beam splitter 47 through the interference filter 46. When the input beam is circular polarization, the S component is reflected by the beam splitter 47 to the path 56, and is applied to the beam splitter 48, then, is applied to the photo-detector 49 through the reflection by the beam splitter 48. The electrical output signal of those path is $E_1$. On the other hand, the P component passes through the beam splitter 47, and is applied to the object A, which attenuates the beam according to the optical transmission factor of the object A. Then, the beam is applied to the beam splitter 54 located at the other side, and is applied to the photo-detector 55 through the path 59. The electrical signal thus obtained is $E_2'$.

Next, at time $t_2$ when the light source 45 is dark, and the light source 51 is bright, the beam of the light source 51 goes along the dotted lines in the figure, and provides the electrical signals $E_2$ at the detector 55, and $E_1'$ at the detector 49.

The above operation is repeated as the light sources 45 and 51 turn ON, and turn OFF.

The optical transmission factor of the object is obtained as follows.

$$(t) = \sqrt{(E_1'E_2')/(E_1E_2)}$$

It should be appreciated that according to the present invention a beam splitter compensates the soil or dust on a beam splitter itself, since a pair of beams 29 and 31 (or 31 and 41) share the common point on a beam splitter.

Figure 7:
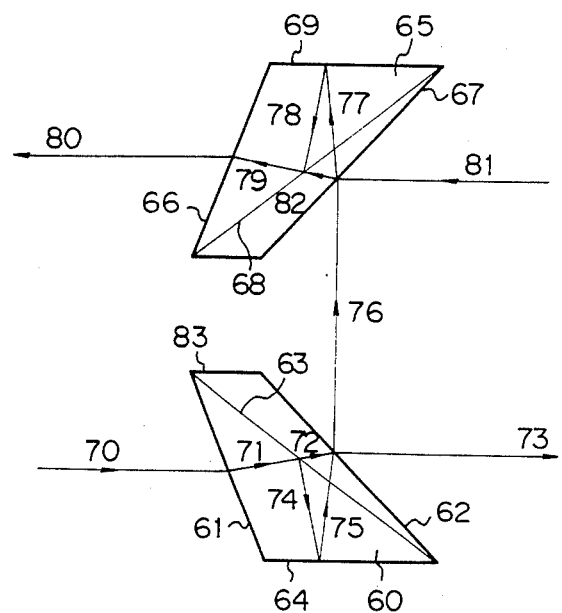
FIG. 7 is a modification of a parallelogramic beam splitter for the use of the present invention.

The other embodiment of the present invention is shown in FIG. 7, which provides the measurement of transmission factor of liquid, although the previous embodiment of FIG. 4 is applicable only to the measurement of air and/or gas.

In FIG. 7, a pair of beam splitters 60 and 65 are shown. The first beam splitter 60 separates an input beam 70 to a pair of perpendicular output beams 73 and 76, and the second beam splitter 65 combines a pair of perpendicular input beams 76 and 81 to a single common output beam 80.

The feature of the embodiment of FIG. 7 in comparing the same with FIG. 4, is that the plane 61 (or 66) is not parallel to the plane 62 (or 67) in FIG. 7. The numerals 63 and 68 in FIG. 7 are polarization film (dielectric film) located along the diagonal plane of the body. The plane 64 and 69 have a mirror surface inside of the plane, as is the case of FIG. 4.

The input beam 70 applied to the polarization film 63 through the path 71 is separated to the P component and the S component. The P component which passes through the polarization film 63 is applied to an object (not shown) through the paths 72 and 73. The S component which is reflected by the polarization film 63 provides the output beam 80 through the paths, 74, 75, 76, 77, 78, and 79. The input beam 81 applied to the beam splitter 65 joins the output beam 80 through the paths 82 and 79.

It should be appreciated in FIG. 7 that the planes 61 and 66 contact with air, and the planes 62 and 67 contact with liquid.

The typical design of the beam splitter in the embodiment of FIG. 7 in case that an object is water is as follows.

The refractive index of a splitter body (glass): 1.684
The angle between plane 61 and polarization film 63; 29°44'
The angle between plane 83 and polarization film 63; 33°57'
The angle between plane 62 and polarization film 63; 11°03'
The angle between plane 64 and polarization film 63; 33°57'

As described above in detail, according to the present invention, a transmission factor is measured accurately even when an apparatus is soiled, by using no mechanical moving means. Since the separation ratio of a beam splitter is improved, the accuracy is considerably improved. Further, the measurement of not only air or gas, but also liquid is possible.

From the foregoing, it will now be apparent that a new and improved measuring apparatus of transmission factor has been discovered. It should be understood of course that the embodiments disclosed are merely illustrative and are not intended to limit the scope of the invention. Reference should be made to the appended claims, therefore, rather than the specification as indicating the scope of the invention.

What is claimed is:

1. A measurement apparatus for measuring optical transmission factor comprising a pair of identical units located at opposing sides of an object to be measured, each unit comprising;
    means for generating a light beam having predetermined restricted wavelength band, the light beams of the respective units being generated alternately,
    a first beam splitter through which passes a P polarization component of said light beam to an object, and offsets a S polarization component,
    a second beam splitter which couples said offset component from said first beam splitter, and a P polarization component from the other unit through said object, to a single common path,
    a photo-detector to receive said two components through said common path to provide two electrical signals relating to intensity of said two components, characterized in that
    said first beam spliter (47, 53,) has at least a first pair of opposing planes (22, 23) for input and output of an optical beam, a second pair of opposing planes (24, 25), and a polarization film (26) located along a diagonal plane of the beam splitter,
    one (24) of said second pair of opposing planes (24, 25) having a mirror surface,
    an input beam (27) to one (22) of said first pair of opposing planes (22, 23) of the beam splitter being split at the polarization film (26) into a transmit beam (28) which is transmitted towards the other (23) of the first pair of opposing planes and a reflect beam (30), which is reflected toward said mirror surface and then toward said other (23) of the first pair of opposing planes,
    said reflect beam (30) sharing a substantially common point (200) on said other plane (23) of said first pair of opposing planes with said transmit beam (28).

2. A measurement apparatus according to claim 1, wherein said second beam splitter has a structure substantially the same as that of said first beam splitter, but with the beams of said second beam splitter travelling in directions opposite to those occurring in said first beam splitter.

3. A measurement apparatus according to claim 2, wherein each of said beam splitters is positioned so that an input beam is applied to the polarization film of the beam splitter with substantially the Brewster angle.

4. A measurement apparatus according to claim 3, wherein difference between angle of incidence of an input beam to the polarization film and the Brewster angle is less than 5 degrees.

5. A measurement apparatus according to claim 1, wherein said first beam splitter is in parallelogram shape.

6. A measurement apparatus according to claim 5, wherein said second beam splitter is in parallelogram shape.

7. A measurement apparatus according to claim 6, wherein each of said beam splitters is made of glass with refraction index 1.684, and the angles between said first pair of parallel opposing planes and the polarization film are 22°12', and the angles between said second pair of opposing planes and the polarization film are 24°48'.

8. A measurement apparatus according to claim 6, wherein each of said beam splitters is made of glass of refraction index 1.684, the angles between the polarization film and the first pair of opposing planes are 29°44' and 11°03', respectively, and the angle between polarization film and each of the second pair of opposing planes is 33°57', and one of said first opposing planes contacts with a liquid in which is the object to be measured.

* * * * *